United States Patent [19]

Guyer et al.

[11] Patent Number: 5,712,382

[45] Date of Patent: Jan. 27, 1998

[54] PLANT ADENYLOSUCCINATE LYASE AND DNA CODING THEREFOR

[75] Inventors: Charles David Guyer; Eric R. Ward, both of Durham, N.C.

[73] Assignee: Novartis Finance Corporation, New York, N.Y.

[21] Appl. No.: 548,509

[22] Filed: Oct. 26, 1995

Related U.S. Application Data

[63] Continuation-in-part of Ser. No. 355,770, Dec. 14, 1994, abandoned.

[51] Int. Cl.$^6$ .................. C12N 15/29; C12N 15/60; C12N 15/63; C12N 1/21; C12N 1/19
[52] U.S. Cl. .................. 536/23.6; 536/23.2; 435/69.1; 435/172.3; 435/232; 435/252.3; 435/254.2; 435/320.1; 435/348
[58] Field of Search .................. 536/23.2, 23.6, 536/24.1; 435/232, 240.2, 252.3, 254.2, 320.1, 69.1, 70.1, 70.3, 71.1, 71.2, 348, 172.3

[56] References Cited

PUBLICATIONS

Casey et al., "Purification of adenylosuccinate lyase from rat skeletal muscle by a novel affinity column: Stabilization of the enzyme, and effects of anions and flouro analogues of the substrate", *Biochem. J.*, 246: 263–269 (1987).

Gendron et al., "Adenylosuccinate lyase of *Bacillus subtilis* regulates the activity of the glutamyl–tRNA synthetase", *Proc. Natl. Acad. Sci., USA*, 89: 5389–5392 (1992).

Schnorr et al., "Molecular characterization of *Arabidopsis thaliana* cDNAs encoding three purine biosynthetic enzymes", *The Plant Journal*, 6(1): 113–121 (1994).

Stone et al., "A mutation in adenylosuccinate lyase associated with mental retardation and autistic features", *Nature Genetics*, 1(1): 59–63 (1992).

Stone et al., "Expression, Purification, and Kinetic Characterization of Recombinant Human Adenylosuccinate Lyase", *J. Biol. Chem.*, 268(26): 19710–19716 (1993).

Aimi et al., "Cloning of a cDNA Encoding Adenylosuccinate Lyase by Functional Complementation in *Escherichia coli*", *J. Biol. Chem.* 265(16): 9011–9014 (1990).

Carter et al., "The Preparation and Properties of Adenylo–Succinase and Adenylosuccinic Acid", *J. Biol. Chem.* 222: 17–30 (1956).

D'Ovidio et al., "Rapid and efficient detection of genetic polymorphism in wheat through amplification by polymerase chain reaction", *Plant Mol. Biol.* 15: 169–171 (1990).

Ebbole et al., "Cloning and Characterization of a 12–Gene Cluster from *Bacillus subtilis* Encoding Nine Enzymes for de Novo Purine Nucleotide Synthesis", *J. Biol. Chem.* 262(17): 8274–8287 (1987).

Frisch et al., "Direct genetic selection of a maize cDNA for dihydrodipicolinate synthase in an *Escherichia coli* dapA$^-$auxotroph", *Mol. Gen. Genet.* 228: 287–293 (1991).

He et al., "*Escherichia coli* purB Gene: Cloning, Nucleotide Sequence, and Regulation by purR", *J. Bacteriol.* 174(1): 130–136 (1992).

Helentjaris et al., "Restriction fragment polymorphisms as probes for plant diversity and their development as tools for applied plant breeding", *Plant Mol. Biol.* 5: 109–118 (1985).

Helentjaris, "A genetic linkage map for maize based on RFLPs", *Trends Genet.* 3(8): 217 (1987).

Niyogi et al., "Suppressors of trp1 Fluorescence Identify a New Arabidopsis Gene, TRP4, Encoding the Anthranilate Synthase β Subunit", *Plant Cell* 5: 1011–1027 (1993).

Pinto et al., "Adenylosuccinate Lyase from Artemia Embryos", *J. Biol. Chem.* 258(20): 12513–12519 (1983).

Senecoff et al., "Isolating the *Arabidopsis thaliana* Genes for de Novo Purine Synthesis by Suppression of *Escherichia coli* Mutants", *Plant Physiol.* 102: 387–399 (1993).

Snustad et al., "Maize Glutamine Synthetase cDNAs: Isolation by Direct Genetic Selection in *Escherichia coli*", *Genetics* 120: 1111–1124 (1988).

Sommer et al., "PCR Amplification of Specific Alleles (PASA) is a General Method for Rapidly Detecting Known Single–Base Changes", *Biotechniques* 12(1): 82 (1992).

*Primary Examiner*—David T. Fox
*Attorney, Agent, or Firm*—J. Timothy Meigs

[57] ABSTRACT

The present invention provides novel plant DNA sequences coding for native adenylosuccinate lyase (ADSL). Methods for using the complete or partial ADSL coding sequence as a probe for diagnostic, mapping and other purposes are taught. Generation of transformed host cells capable of expressing ADSL is also taught. Methods of using the transformed host cells are taught, including methods for recombinant production of ADSL enzymes. A method for using the plant ADSL enzyme to screen for inhibitors of ADSL activity is also provided.

18 Claims, No Drawings

PLANT ADENYLOSUCCINATE LYASE AND DNA CODING THEREFOR

This application is a Continuation-in-Part of U.S. Ser. No. 08/355,770, filed Dec. 14, 1994, now abandoned, which disclosures are herein incorporated in their entirety.

FIELD OF THE INVENTION

The invention relates generally to a plant enzymatic activity involved in the biosynthesis of adenosine 5'-monophosphate (AMP). The invention particularly relates to the plant enzyme and gene coding therefor which catalyzes two biochemical reactions; (1) the synthesis of 5'-phosphoribosyl-4-carboxamide-5-aminoimidazole (AICAR) from 5'-phosphoribosyl-4-(N-succinocarboxamide)-5-aminoimidazole (SAICAR), and (2) the final reaction in the two step sequence from inosine 5'-monophosphate (IMP) to AMP. The invention relates to various utilities including the recombinant production of this enzyme in a heterologous host, screening chemicals for herbicidal activity, and the development of genetic markers in plants.

BACKGROUND OF THE INVENTION

I. The ADSL Enzyme and its Involvement in the AMP and IMP Biosynthetic Pathways One of the enzymes essential to the biosynthesis of AMP in plants is known as adenylosuccinate lyase (referred to herein as "ADSL"). The ADSL enzyme is typically about 52Kd and catalyzes the final reaction in the two step reaction sequence which converts inosine 5'-monophosphate (IMP) to AMP. ADSL also catalyzes an essential step in the biosynthesis of IMP, the synthesis of 5'-phosphoribosyl-4-carboxamide-5-aminoimidazole (AICAR) from 5'-phosphoribosyl-4-(N-succinocarboxamide)-5-aminoimidazole (SAICAR) (step 8 in the IMP biosynthetic pathway). In addition to acting as a precursor to AMP, IMP is also the mediate precursor of guanosine 5'-monophosphate (GMP).

Genes encoding the ADSL enzyme have heretofore not been isolated and characterized from any plant species. However, genes encoding the ADSL enzyme have been isolated from a variety of non-plant species including *E. coli* (He et al., *J. Bacteriol.* 174: 130–136 (1992)), *Bacillus subtilis* (Ebbole and Zalkin, *J. Biol. Chem.* 262: 8274–8287 (1987)), chicken (Aimi et al, *J. Biol Chem.* 265: 9011–9014 (1990)), human (Genbank accession no. X65867), and *Spiroplasma citri* (Genbank accession no. L22971).

Presently, too little is known about the plant ADSL enzyme and its relationship to the ADSL enzymes/genes which have been isolated from other organisms to allow isolation of ADSL encoding genes from any plant species using known approaches.

In particular, many of the standard techniques for isolation of new proteins and genes are based upon the assumption that they will be significantly similar in primary structure (i.e. amino acid and DNA sequence) to known proteins and genes that have the same function. Such standard techniques include nucleic acid hybridization and amplification by polymerase chain reaction using oligonucleotide primers corresponding to conserved amino acid sequence motifs. These techniques would not be expected to be useful for isolation of plant ADSL genes using presently available structural information limited to ADSL genes from non-plant organisms since there is no significant structural similarity even among the known ADSL genes and proteins.

Another approach that has been used to isolate biosynthetic genes in other metabolic pathways from higher eukaryotes is the complementation of microbial mutants deficient in the activity of interest (see, e.g. Niyogi et al., *Plant Cell* 5: 1011 (1993); Senecoff and Meagher, *Plant Physiol.* 102: 387–399 (1993); Snustad et al, *Genetics* 120:1111–1114 (1988); Frisch et al., *Mol. Gen. Genet.* 228:287–293(1991)). For this approach, a library of cDNAs from the higher eukaryote is cloned in a vector that can direct expression of the cDNA in the microbial host. The vector is then transformed or otherwise introduced into the mutant microbe, and colonies are selected that are phenotypically no longer mutant.

Unfortunately, this approach does not appear to be useful for the isolation of a plant ADSL gene based on a previously reported attempt (Senecoff and Meagher, supra). This article reported the complementation of an *E. coli* purine auxotrophic strain purported to be deficient in ADSL (strain no. TX530) with an *Arabidopsis thaliana* cDNA library. However, this article failed to identify any cDNA clone encoding a plant ADSL. Moreover, repeated complementation of the same strain used in this article (strain no. TX530) with a cDNA library resulted in the identification of cDNA clones encoding an AIR synthetase rather than an ADSL.

SUMMARY OF THE INVENTION

The present invention provides an isolated DNA molecule encoding the adenylosuccinate lyase (ADSL) enzyme from a plant source.

A DNA coding sequence for an ADSL enzyme in *Arabidopsis thaliana* is provided in SEQ ID NOS: 1 and 3. A DNA coding sequence for an ADSL enzyme in *Zea mays* (i.e. maize) is provided in SEQ ID No. 4. Using the information provided by the present invention, the DNA coding sequence for the adenylosuccinate lyase (ADSL) enzyme(s) from any plant source may be obtained using standard methods.

The present invention also embodies the recombinant production of the ADSL enzyme, and methods for using recombinantly produced ADSL. In particular, the present invention provides methods of using purified ADSL to screen for novel inhibitors of ADSL activity which may be used as herbicides to control undesirable vegetation in fields where crops are grown, particularly agronomically important crops such as maize and other cereal crops such as wheat, oats, rye, sorghum, rice, barley, millet, turf and forage grasses, and the like, as well as cotton, sugar cane, sugar beet, oilseed rape, and soybeans.

The present invention is further directed to probes and methods for detecting the presence and form of the ADSL gene and quantitating levels of ADSL transcripts in an organism. These methods may be used to diagnose plant disease conditions which are associated with an altered form of the ADSL enzyme or altered levels of expression of the ADSL enzyme.

DETAILED DESCRIPTION OF THE INVENTION

In one aspect, the present invention is directed to an isolated DNA molecule which encodes a plant adenylosuccinate lyase (referred to herein as "ADSL"), the enzyme which catalyzes a step in the biosynthesis of IMP and a step in the conversion of IMP to AMP. The DNA coding sequence and corresponding amino acid sequence for one ADSL enzyme from *Arabidopsis thaliana* is provided as SEQ ID NOS: 1 and 2, respectively. A partial cDNA coding for a second ADSL gene from *Arabidopsis thaliana* is set forth in SEQ ID No. 3. The DNA coding sequence and corresponding amino acid sequence for an ADSL enzyme from maize is provided as SEQ ID NOS: 4 and 5, respectively.

The DNA encoding the ADSL enzyme may be isolated from the genome of any plant species desired according to the invention. One method taught for isolating a plant ADSL coding sequence is represented by Example 1 (see also U.S. patent application Ser. No. 08/236,427, filed Apr. 29, 1994 to Ward et al., now U.S. Pat. No. 5,541,310, incorporated by reference herein in its entirety). In this method cDNA clones encoding an ADSL enzyme are identified from a library of cDNA clones derived from the eukaryote of interest based on their ability to supply ADSL enzymatic activity to a mutant host organism deficient in this activity. Suitable host organisms for use in this method are those which can be used to screen cDNA expression libraries and for which mutants deficient in ADSL activity are either available or can be routinely generated. Such host organisms include, but are not limited to, *E. coli* purB (strain no. JK268) and yeast ade13 (Doffman, *Genetics* 61:377–389 (1969)) routants.

Alternatively, plant ADSL coding sequences may be isolated according to well known techniques based on their sequence homology to the *Arabidopsis thaliana* or maize ADSL coding sequences set forth in SEQ ID NOS: 1, 3 and 4. In these techniques all or part of the known ADSL coding sequence is used as a probe which selectively hybridizes to other ADSL coding sequences present in population of cloned genomic DNA fragments or cDNA fragments (i.e. genomic or cDNA libraries) from a chosen organism. Such techniques include hybridization screening of plated DNA libraries (either plaques or colonies; see, e.g.. Sambrook et al., *Molecular Cloning*, eds., Cold Spring Harbor Laboratory Press. (1989)) and amplification by PCR using oligonucleotide primers corresponding to sequence domains conserved among known ADSL amino acid sequences (see, e.g. Innis et al.,. *PCR Protocols, a Guide to Methods and Applications* eds., Academic Press (1990)). These methods are particularly well suited to the isolation of ADSL coding sequences from organisms closely related to the organism from which the probe sequence is derived. Thus, application of these methods using the Arabidopsis or maize coding sequence as a probe would be expected to be particularly well suited for the isolation of ADSL coding sequences from other plant species including monocotyledenous and dicotyledenous species, and more particularly those species most closely related to either maize in the Gramineae family or *Arabidopsis thaliana* in the Cruciferae family.

The isolated plant ADSL sequences taught by the present invention may be manipulated according to standard genetic engineering techniques to suit any desired purpose. For example, the entire ADSL sequence or portions thereof may be used as probes capable of specifically hybridizing to ADSL coding sequences and messenger RNAs. To achieve specific hybridization under a variety of conditions, such probes include sequences that are unique among ADSL coding sequences and are preferably at least 10 nucleotides in length, and most preferably at least 20 nucleotides in length. Such probes may be used to amplify and analyze ADSL coding sequences from a chosen organism via the well known process of polymerase chain reaction (PCR). This technique may be used to isolate additional ADSL coding sequences from a desired organism or as a diagnostic assay to determine the presence of ADSL coding sequences in an organism and to associate altered coding sequences with particular adverse conditions, such as severe autism (Aimi, J. et al., *J. Biol. Chem.* 265: 9011–9014 (1990)).

ADSL specific hybridization probes may also be used to map the location of the native ADSL gene(s) in the genome of a chosen plant using standard techniques based on the selective hybridization of the probe to genomic ADSL sequences. These techniques include, but are not limited to, identification of DNA polymorphisms identified or contained within the ADSL probe sequence, and use of such polymorphisms to follow segregation of the ADSL gene relative to other markers of known map position in a mapping population derived from self fertilization of a hybrid of two polymorphic parental lines (see e.g. Helentjaris et al., *Plant Mol. Biol.* 5: 109 (1985). Sommer et al. *Biotechniques* 12:82 (1992); D'Ovidio et al., *Plant Mol. Biol.* 15: 169 (1990)). While any plant ADSL sequence is contemplated to be useful as a probe for mapping ADSL genes, preferred probes are those ADSL sequences from plants more closely related to the chosen plant, and most preferred probes are those ADSL sequences from the chosen plant. Mapping of ADSL genes in this manner is contemplated to be particularly useful for breeding purposes. For instance, by knowing the genetic map position of a mutant ADSL gene that confers herbicide resistance, flanking DNA markers can be identified from a reference genetic map (see, e.g., Helentjaris, *Trends Genet.* 3: 217 (1987)). During introgression of the herbicide resistance trait into a new breeding line, these markers can then be used to monitor the extent of ADSL-linked flanking chromosomal DNA still present in the recurrent parent after each round of backcrossing.

ADSL specific hybridization probes may also be used to quantitate levels of ADSL mRNA in a plant using standard techniques such as Northern blot analysis. This technique may be used as a diagnostic assay to detect altered levels of ADSL expression that may be associated with particular adverse conditions such as severe antism (Aimi, J. et al., *J. Biol. Chem.* 265: 9011–9014 (1990)).

For recombinant production of the enzyme in a host organism, the plant ADSL coding sequence may be inserted into an expression cassette designed for the chosen host and introduced into the host where it is recombinantly produced. The choice of specific regulatory sequences such as promoter, signal sequence, 5' and 3' untranslated sequences, and enhancer appropriate for the chosen host is within the level of skill of the routineer in the art. The resultant molecule, containing the individual elements linked in proper reading frame, may be inserted into a vector capable of being transformed into the host cell. Suitable expression vectors and methods for recombinant production of proteins are well known for host organisms such as *E. coli* (see, e.g. Studier and Moffatt, *J. Mol. Biol.* 189: 113 (1986); Brosius, DNA 8: 759 (1989)), yeast (see, e.g., Schneider and Guarente, *Meth. Enzymol.* 194: 373 (1991)) and insect cells (see, e.g., Luckow and Summers, Bio/Technol. 6: 47 (1988)). Specific examples include plasmids such as pBluescript (Stratagene, La Jolla, Calif.), pFLAG (International Biotechnologies, Inc., New Haven, Conn.), pTrcHis (Invitrogen, La Jolla, Calif.), and baculovirus expression vectors, e.g., those derived from the genome of *Autographica californica* nuclear polyhedrosis virus (AcMNPV). A preferred baculovirus/insect system is pV111392/Sf21 cells (Invitrogen, La Jolla, Calif.).

Recombinantly produced plant ADSL enzyme can be isolated and purified using a variety of standard techniques. The actual techniques which may be used will vary depending upon the host organism used, whether the ADSL enzyme is designed for secretion, and other such factors familiar to the skilled artisan (see, e.g. chapter 16 of Ausubel, F. et al., "Current Protocols in Molecular Biology", pub. by John Wiley & Sons, Inc. (1994).

Recombinantly produced plant ADSL enzyme is useful for a variety of purposes. For example, it may be used to supply ADSL enzymatic activity in vitro to synthesize 5'-phosphoribosyl-4-carboxamide-5-aminoimidazole (AICAR) or to convert IMP to AMP. It may also be used as a substitute for ADSL purified from yeast which is sold commercially (e.g. Sigma Chemical Co., St. Louis, Mo., 1994 catalog no. A4653).

Recombinantly produced plant ADSL enzyme may also be used in an in vitro assay to screen known herbicidal chemicals whose target has not been identified to determine if they inhibit ADSL. Such an in vitro assay may also be used as a more general screen to identify chemicals which inhibit ADSL activity and which are therefore herbicide candidates. Alternatively, recombinantly produced ADSL may be used to elucidate the complex structure of this enzyme. Such information regarding the structure of the ADSL enzyme may be used, for example, in the rational design of new inhibitory herbicides.

The inhibitory effect on ADSL may be determined in an in vitro assay by monitoring the inhibition of transformation of adenylosuccinate to AMP catalyzed by ADSL. Typical in vitro conditions for this reaction are 50 mm Tris-HCl buffer, pH7.5, 0.025 mM EDTA, 0.015 mM adenylosuccinate, and enzyme (Pinto et al., *J. Biol. Chem.* 258: 12513–12519)). Transformation of adenylosuccinate to AMP is measured as a decrease in $A_{280}$ (Carter and Cohen, *J. Biol. Chem.* 222:17–30 (1956)).

The invention will be further described by reference to the following detailed examples. These examples are provided for purposes of illustration only, and are not intended to be limiting unless otherwise specified.

EXAMPLES

Standard recombinant DNA and molecular cloning techniques used here are well known in the art and are described by T. Maniatis, E. F. Fritsch and J. Sambrook, *Molecular Cloning: A Laboratory manual*, Cold Spring Harbor laboratory, Cold Spring Harbor, N.Y. (1982) and by T. J. Silhavy, M. L. Berman, and L. W. Enquist, *Experiments with Gene Fusions*, Cold Spring Harbor Laboratory, Cold Spring Harbor, N.Y. (1984) and by Ausubel, F.M. et al., *Current Protocols in Molecular Biology*, pub. by Greene Publishing Assoc. and Wiley-Interscience (1987).

Example 1

Isolation of Arabidopsis cDNAs Encoding ADSL Genes by Complementation of an *E. coli* Mutant A cDNA encoding adenylosuccinate lyase from *Arabidopsis thaliana* was isolated by functional complementation of the *E. coli* purB mutant JK268 supplied by Howard Zalkin (Dept. of Biochemistry, Purdue Univ.). Plasmid DNA of a cDNA library of Arabidopsis mRNA cloned in the expression vector pFL61 (Minet et al. (1992) Plant J. 2: 417–422) was transformed into JK268 by electropotation using the Bio-Rad Gene Pulser. The cells were plated on M9 minimal agar (J. Miller, Experiments in Molecular Genetics, Cold Spring Harbour, (1970) containing 100 mg/ml ampicillin and supplemented with 0.4% casamino acids, 0.2 ug/ml thiamin, 50 ug/ml tryptophan at a density of approximately $1\times10^6$ transformants/10 cm plate. Plates were incubated at 37° C. for 40 hours. Adenine prototrophs were recovered at a frequency of $2/10^5$. Plasmid DNA was purified from 10 purine prototrophic colonies and all were shown to recomplement the original auxotrophic mutant JK268 at high frequency indicating that all of these clones encoded functional ADSL enzyme.

A restriction digest of the 10 clones revealed 2 size classes of approximately 3.0 and 3.4 kb. Sequencing data revealed they all represented the same cDNA and all were chimaeric. A database search of the longest clone using the GAP program (Deveraux et al., Nucleic Acids Res. 12:387–95 (1984), revealed homology with the ADSL from *E. coli*. The proteins are 75% similar and 60% identical. The coding sequence of the mature protein and an incomplete chloroplast transit peptide begins approximately 1.8 kb from the 3' end of the chimaeric clone.

A full-length cDNA designated ADSL-1 and a 450 bp cDNA fragment representing a second distinct gene, designated herein as ADSL-2, was obtained from an *Arabidopsis thaliana* lambda ZAP library using the initial clone as a probe. The ADSL-1 and ADSL-2 sequences are 72% identical over the corresponding nucleotides.

ADSL-1, in the pBluescript SK vector, was deposited Jul. 28, 1994 as pDG-1a.t.(NRRL #B-21298).

ADSL-2, in the pBluescfipt SK vector, was deposited Oct. 14, 1994 as pDG-2a.t. (NRRL#B-21348).

The Arabidopsis cDNA sequences encoding ADSL-l(full-length) and ADSL-2(partial) are set forth in SEQ ID NOS: 1 and 3, respectively.

Example 2

Isolation of Additional ADSL Genes Based on Sequence Homology to known ADSL Coding Sequences A phage or plasmid cDNA library is plated at a density of approximately 10,000 plaques on a 10 cm Petri dish, and filter lifts of the plaques are made after overnight growth of the plates at 37 C. The plaque lifts are probed with one of the cDNAs set forth in SEQ ID NOS: 1 or 3, labeled with 32P-dCTP by the random priming method by means of a PrimeTime kit (International Biotechnologies, Inc., New Haven, Conn.). Hybridization conditions are 7% sodium dodecyl sulfate (SDS), 0.5M NaPO4 pH 7.0, 1 mM EDTA at 50 C. After hybridization overnight, the filters are washed with 2X SSC, 1% SDS. Positively hybridizing plaques are detected by autoradiography. After purification to single plaques, cDNA inserts are isolated, and their sequences determined by the chain termination method using dideoxy terminators labeled with fluorescent dyes (Applied Biosystems, Inc., Foster City, Calif.).

The standard experimental protocol described above can be used by one of skill in the art to obtain ADSL genes sequentially homologous to the known ADSL coding sequences from any other eukaryote, particularly other higher plant species. This protocol is particularly useful for obtaining ADSL genes which share 50% or greater homology to the ADSL coding sequence used as a probe.

Applicability of this protocol for obtaining ADSL genes from other plants has been supported by the observation of specific hybridization of an Arabidopsis ADSL coding sequence probe to discrete DNA restriction fragments from the *Zea mays* genome in a standard Southern blot This result indicates that the degree of homology between the Arabidopsis and *Zea mays* ADSL coding sequences is sufficient for the Arabidopsis sequence to specifically hybridize to the *Zea mays* sequence present among a pool of DNA representing the entire maize genome. In view of this Southern result, specific hybridization of the Arabidopsis ADSL coding sequence to a maize cDNA library according to the protocol above would be expected since such a library represents only a subset of the entire maize genomic DNA (i.e. the coding portion)

Example 3

Isolation of a Maize cDNA Encoding ADSL by Functional Complementation of an *E. coli* mutant.

A cDNA encoding adenylosuccinate lyase from maize was isolated by functional complementation of the *E. coli* purB mutant JIC268 supplied by Howard Zalkin (Dept. of Biochemistry, Purdue Univ.). Plasmid DNA of a cDNA library of maize mRNA cloned in the vector pBS (Stratagene) was transformed into JK268 by electropotation using the Bio-Rad Gene Pulser. The cells were plated on M9 minimal agar (J. Miller, Experiments in Molecular Genetics, Cold Spring Harbour, 1970) containing 100mg/ml ampicillin and supplemented with 0.4% casamino acids, 0.2ug/ml thiamin, 50ug/mi tryptophan at a density of approximately $1\times10^6$ transformants/10cm plate. Plates were incubated at 37° C. for 40 hours.

Adenine prototrophs were recovered at a frequency of $4/10^7$. Plasmid DNA was purified from 6 purine prototrophic colonies. One clone was shown to recomplement the original auxotrophic mutant JK268 at a high frequency, indicating that this clone encodes a functional ADSL enzyme.

Sequencing data indicated the 1659 bp cDNA, designated MASL-1, represented the coding sequence of the mature protein and an incomplete choroplast transit peptide. A comparison of the maize and Arabidopsis ADSL proteins using the GAP program revealed significant amino acid sequence homology; these proteins are 74% similar and 59% identical.

MASL-1, in the pBluescript SK vector was deposited Aug. 18, 1995 as pDG-5a.t. (NRRL #B-21494).

The maize cDNA sequence encoding MASL-1 and corresponding amino acid sequence is set forth in SEQ ID NOS: 4 and 5, respectively.

Various modifications of the invention described herein will be apparent to those skilled in the art. Such modifications are intended to fall within the scope of the appended claims.

---

We claim:

1. An isolated DNA molecule encoding a protein from an Arabidopsis plant having adenylosuccinate lyase(ADSL) activity, wherein said DNA molecule encodes a protein comprising the amino acid sequence set forth in SEQ ID No. 2.

2. The isolated DNA molecule of claim 1, wherein said DNA molecule comprises the nucleotide sequence set forth in SEQ ID No. 1.

3. An isolated DNA molecule encoding a protein from a maize plant having adenylosuccinate lyase(ADSL) activity.

4. The isolated DNA molecule of claim 3, wherein said DNA molecule encodes a protein comprising the amino acid sequence set forth in SEQ ID No. 5.

5. The isolated DNA molecule of claim 4, wherein said DNA molecule comprises the nucleotide sequence set forth in SEQ ID No.4.

6. A chimeric gene comprising a promoter operably linked to a DNA molecule encoding a protein comprising an amino acid sequence selected from the group consisting of SEQ ID No. 2 and SEQ ID No. 5.

7. A recombinant vector comprising the chimeric gene of claim 6 wherein said vector is capable of being stably transformed into a host cell.

8. A host cell stably transformed with the vector of claim 7 wherein said host cell is capable of expressing said DNA molecule.

9. A host cell of claim 8 selected from the group consisting of a bacterial cell, a yeast cell, and an insect cell.

10. An isolated DNA molecule encoding a protein from a monocotyledenous plant having adenylosuccinate lyase (ADSL) activity.

11. The isolated DNA molecule of claim 10, wherein said monocotyledenous plant is in the Gramineae family.

12. The isolated DNA molecule of claim 11, wherein said monocotyledenous plant is maize.

13. The isolated DNA molecule of claim 10, wherein said DNA molecule hybridizes to the nucleotide sequence set forth in SEQ ID NO:4 under the following conditions: hybridization in 7% sodium dodecyl sulfate (SDS), 0.5M NaPO4 pH 7.0, 1 mM EDTA at 50 C; and wash with 2X SSC, 1% SDS.

14. A chimetic gene comprising a promoter operably linked to the isolated DNA molecule of claim 13.

15. A recombinant vector comprising the chimeric gene of claim 14, wherein said vector is capable of being stably transformed into a host cell.

16. A host cell stably transformed with the vector of claim 15, wherein said host cell is capable of expressing said DNA molecule.

17. A host cell of claim 16 selected from the group consisting of a bacterial cell, a yeast cell, and an insect cell.

18. An isolated DNA molecule that hybridizes to the DNA molecule of claim 2 under the following conditions: hybridization in 7% sodium dodecyl sulfate (SDS), 0.5M NaPO4 pH 7.0, 1 mM EDTA at 50 C; and wash with 2X SSC, 1% SDS; wherein said isolated DNA molecule encodes a plant protein having adenylosuccinate lyase activity.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 1796 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i x ) FEATURE:
        ( A ) NAME/KEY: CDS
        ( B ) LOCATION: 14..1600
        ( D ) OTHER INFORMATION: /product="Arabidopsis Adenylosuccinate Lyase"

( x i ) SEQUENCE DESCRIPTION: SEQ ID NO:1:

```
GGCACGAGCT TCA ATG GCT ATA ACA CAC CCC AAA ATC CCT TCT TTC GGT          49
            Met Ala Ile Thr His Pro Lys Ile Pro Ser Phe Gly
             1           5                   10

TTT ACA CCC ACC GGA ATA TTC CTA AAC CCA TCA AAA TCA GTG TGT TTG         97
Phe Thr Pro Thr Gly Ile Phe Leu Asn Pro Ser Lys Ser Val Cys Leu
         15              20              25

GCT TCA CAT CAT CGG CTT CCG AGA GTT TCA TGC TCT GTT TCT ACT ACT        145
Ala Ser His His Arg Leu Pro Arg Val Ser Cys Ser Val Ser Thr Thr
     30              35              40

ACT GAT TCT CCC AAG CTA GTG ACT TCA ACA AAG GTG ACG GCA ATG GAT        193
Thr Asp Ser Pro Lys Leu Val Thr Ser Thr Lys Val Thr Ala Met Asp
 45              50              55              60

GGA GTG AGC TCT AGA GAC TTG GAG ATG TCG AAT TTA ACG GCG TTA TCG        241
Gly Val Ser Ser Arg Asp Leu Glu Met Ser Asn Leu Thr Ala Leu Ser
             65              70              75

CCT TTG GAT GGA CGT TAT TGG AGT AAA GTT AAG GAC TTG GCT TCT TCT        289
Pro Leu Asp Gly Arg Tyr Trp Ser Lys Val Lys Asp Leu Ala Ser Ser
```

-continued

```
                    80                              85                              90
TTG AGC GAG TTT GGA TTG ATC TAT TTC CGA GTT TTT GTC GAG ATC AAA                 337
Leu Ser Glu Phe Gly Leu Ile Tyr Phe Arg Val Phe Val Glu Ile Lys
        95                          100                     105

TGG CTT CTT AAG CTT TCG AAT ATT CCT GAA GTC ACT GAA GTT CCA AGC                 385
Trp Leu Leu Lys Leu Ser Asn Ile Pro Glu Val Thr Glu Val Pro Ser
    110                     115                     120

TTT AGC AAA GAA GCT CAG AGT TTC TTG CAA GGC ATA ATC GAT GGA TTT                 433
Phe Ser Lys Glu Ala Gln Ser Phe Leu Gln Gly Ile Ile Asp Gly Phe
125                     130                     135                     140

AGC ATA GAC GAT GCA TTG GAA ATT AAG AAG ATT GAG AGA GTA ACA AAT                 481
Ser Ile Asp Asp Ala Leu Glu Ile Lys Lys Ile Glu Arg Val Thr Asn
                145                     150                     155

CAT GAT GTG AAA GCA GTG GAG TAT TTC TTG AAA CAA AAG TGT GAA TCA                 529
His Asp Val Lys Ala Val Glu Tyr Phe Leu Lys Gln Lys Cys Glu Ser
            160                     165                     170

CAA CCA GAG ATT GCT AAG GTT CTT GAG TTT TTC CAT TTC GCT TGC ACG                 577
Gln Pro Glu Ile Ala Lys Val Leu Glu Phe Phe His Phe Ala Cys Thr
        175                     180                     185

TCT GAG GAC ATC AAC AAT CTT TCC CAT GCT TTG ATG CTT CAA GAA GCA                 625
Ser Glu Asp Ile Asn Asn Leu Ser His Ala Leu Met Leu Gln Glu Ala
    190                     195                     200

CTT AGT TCG GTT ATA CTT CCT ACC ATG GAT GAG CTG ATC AAG TCA ATC                 673
Leu Ser Ser Val Ile Leu Pro Thr Met Asp Glu Leu Ile Lys Ser Ile
205                     210                     215                     220

TCT CTG ATA GCT AAG AAC TTT GCT TAT GTC CCC ATG CTT TCA CGA ACT                 721
Ser Leu Ile Ala Lys Asn Phe Ala Tyr Val Pro Met Leu Ser Arg Thr
                225                     230                     235

CAT GGG CAG CCA GCT ACG CCA ACA ACT TTG GGG AAA GAA ATG GCG AAT                 769
His Gly Gln Pro Ala Thr Pro Thr Thr Leu Gly Lys Glu Met Ala Asn
            240                     245                     250

TTT GCT GTG AGG TTA AGC GAA GAA AGG AGA TAT CTT TCA GAA ACT AAG                 817
Phe Ala Val Arg Leu Ser Glu Glu Arg Arg Tyr Leu Ser Glu Thr Lys
        255                     260                     265

ATT AAG GGG AAA TTT GCA GGT GCT GTT GGG AAC TAC AAC GCC CAT ATT                 865
Ile Lys Gly Lys Phe Ala Gly Ala Val Gly Asn Tyr Asn Ala His Ile
    270                     275                     280

TCC GCA TAT TCG AAT ATT GAC TGG CCT CAT GTT TCC GAG GAG TTT GTT                 913
Ser Ala Tyr Ser Asn Ile Asp Trp Pro His Val Ser Glu Glu Phe Val
285                     290                     295                     300

ACT TCT CTT GGA TTA ACA TTC AAC CCA TAC GTG ACT CAG ATT GAA CCT                 961
Thr Ser Leu Gly Leu Thr Phe Asn Pro Tyr Val Thr Gln Ile Glu Pro
                305                     310                     315

CAT GAC TAT ATG GCT AGA CTT TTT AAT AAT ATC AGC CAG TTC AAC ACT                 1009
His Asp Tyr Met Ala Arg Leu Phe Asn Asn Ile Ser Gln Phe Asn Thr
            320                     325                     330

ATT TTA ATT GAT TTT GAC AGA GAT ATA TGG AGC TAC ATA TCT CTA GGG                 1057
Ile Leu Ile Asp Phe Asp Arg Asp Ile Trp Ser Tyr Ile Ser Leu Gly
        335                     340                     345

TAC TTT AAG CAG ACA ACT AAA GCG GGT GAA ATT GGA TCG TCG ACA ATG                 1105
Tyr Phe Lys Gln Thr Thr Lys Ala Gly Glu Ile Gly Ser Ser Thr Met
    350                     355                     360

CCT CAC AAA GTG AAT CCT ATT GAC TTT GAG AAC AGC GAA GGG AAT CTA                 1153
Pro His Lys Val Asn Pro Ile Asp Phe Glu Asn Ser Glu Gly Asn Leu
365                     370                     375                     380

GGG AAA GCA AAC GCA GAG CTT ACT TTT CTC AGC ATG AAG CTT CCC ATT                 1201
Gly Lys Ala Asn Ala Glu Leu Thr Phe Leu Ser Met Lys Leu Pro Ile
                385                     390                     395

TCA CGC ATG CAG CGT GAT TTA ACT GAT TCA ACT GTC TTG AGA AAC ATG                 1249
Ser Arg Met Gln Arg Asp Leu Thr Asp Ser Thr Val Leu Arg Asn Met
```

|  |  |  |  |  |  |  |  |  |  |  |  |  |  |  |  |
|--|--|--|--|--|--|--|--|--|--|--|--|--|--|--|--|
|  |  |  | 400 |  |  |  |  | 405 |  |  |  |  | 410 |  |  |
| GGT | GGA | GCT | TTA | GGA | CAC | TCT | CTT | CTC | GCT | TAC | AAG | AGT | GCG | ATA | CAG | 1297 |
| Gly | Gly | Ala | Leu | Gly | His | Ser | Leu | Leu | Ala | Tyr | Lys | Ser | Ala | Ile | Gln |
|  |  | 415 |  |  |  |  | 420 |  |  |  |  | 425 |  |  |  |
| GGA | ATC | GGG | AAG | CTT | CAG | GTT | AAT | GAA | GCT | CGG | TTA | AAA | GAA | GAT | TTG | 1345 |
| Gly | Ile | Gly | Lys | Leu | Gln | Val | Asn | Glu | Ala | Arg | Leu | Lys | Glu | Asp | Leu |
|  |  | 430 |  |  |  |  | 435 |  |  |  |  | 440 |  |  |  |
| GAT | GAT | AAT | TGG | GAA | GTC | CTT | GCT | GAA | CCA | ATA | CAA | ACT | GTG | ATG | AGG | 1393 |
| Asp | Asp | Asn | Trp | Glu | Val | Leu | Ala | Glu | Pro | Ile | Gln | Thr | Val | Met | Arg |
| 445 |  |  |  |  | 450 |  |  |  |  | 455 |  |  |  |  | 460 |
| AGA | TAC | GGT | GTC | CCT | GAG | CCG | TAT | GAG | AAG | CTG | AAG | GAG | CTA | ACA | AGA | 1441 |
| Arg | Tyr | Gly | Val | Pro | Glu | Pro | Tyr | Glu | Lys | Leu | Lys | Glu | Leu | Thr | Arg |
|  |  |  |  | 465 |  |  |  |  | 470 |  |  |  |  | 475 |  |
| GGA | AAA | GCT | GTG | AAT | GAA | GAA | ACC | ATA | AGA | ACG | TTT | ATC | AAA | GGT | TTG | 1489 |
| Gly | Lys | Ala | Val | Asn | Glu | Glu | Thr | Ile | Arg | Thr | Phe | Ile | Lys | Gly | Leu |
|  |  |  | 480 |  |  |  |  | 485 |  |  |  |  | 490 |  |  |
| GAA | TTG | CCT | TCA | GAA | GCA | AAA | GAC | CAA | CTT | CTG | GAG | CTA | ACT | CCA | CAC | 1537 |
| Glu | Leu | Pro | Ser | Glu | Ala | Lys | Asp | Gln | Leu | Leu | Glu | Leu | Thr | Pro | His |
|  |  | 495 |  |  |  |  | 500 |  |  |  |  | 505 |  |  |  |
| ACA | TAT | GTT | GGT | GCT | GCT | GCT | GCA | TTG | GCA | CTG | GCC | GTG | GAT | GAA | GCT | 1585 |
| Thr | Tyr | Val | Gly | Ala | Ala | Ala | Ala | Leu | Ala | Leu | Ala | Val | Asp | Glu | Ala |
|  |  | 510 |  |  |  |  | 515 |  |  |  |  | 520 |  |  |  |
| CTG | CAC | TTG | GGA | CAT | TGATGATGAT | CAAAGTGGTG | ATAGATTGTC | CTCTTTTATT |  |  |  |  |  |  |  | 1640 |
| Leu | His | Leu | Gly | His |  |  |  |  |  |  |  |  |  |  |  |
| 525 |  |  |  |  |  |  |  |  |  |  |  |  |  |  |  |

ATGGTATTCT TYTCGAAATT GGTGGAAAAC AGAGACAATT TATAGGTCGG TGACTTGCAA    1700

GTCGTCGTTT AAAATGTTAA GAAAAATCTT GTACCATTGT TGTGTTATGT TTCCTCTTTG    1760

AGTGTCTGTG TTTTATCTAA AAAAAAAAAA AAAAA                               1796

( 2 ) INFORMATION FOR SEQ ID NO:2:

( i ) SEQUENCE CHARACTERISTICS:
        ( A ) LENGTH: 529 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Ala | Ile | Thr | His | Pro | Lys | Ile | Pro | Ser | Phe | Gly | Phe | Thr | Pro | Thr |
|--|--|--|--|--|--|--|--|--|--|--|--|--|--|--|--|
| 1 |  |  |  | 5 |  |  |  |  | 10 |  |  |  |  | 15 |  |
| Gly | Ile | Phe | Leu | Asn | Pro | Ser | Lys | Ser | Val | Cys | Leu | Ala | Ser | His | His |
|  |  |  | 20 |  |  |  |  | 25 |  |  |  |  | 30 |  |  |
| Arg | Leu | Pro | Arg | Val | Ser | Cys | Ser | Val | Ser | Thr | Thr | Thr | Asp | Ser | Pro |
|  |  |  | 35 |  |  |  |  | 40 |  |  |  |  | 45 |  |  |
| Lys | Leu | Val | Thr | Ser | Thr | Lys | Val | Thr | Ala | Met | Asp | Gly | Val | Ser | Ser |
|  | 50 |  |  |  |  | 55 |  |  |  |  | 60 |  |  |  |  |
| Arg | Asp | Leu | Glu | Met | Ser | Asn | Leu | Thr | Ala | Leu | Ser | Pro | Leu | Asp | Gly |
| 65 |  |  |  |  | 70 |  |  |  |  | 75 |  |  |  |  | 80 |
| Arg | Tyr | Trp | Ser | Lys | Val | Lys | Asp | Leu | Ala | Ser | Ser | Leu | Ser | Glu | Phe |
|  |  |  |  | 85 |  |  |  |  | 90 |  |  |  |  | 95 |  |
| Gly | Leu | Ile | Tyr | Phe | Arg | Val | Phe | Val | Glu | Ile | Lys | Trp | Leu | Leu | Lys |
|  |  |  | 100 |  |  |  |  | 105 |  |  |  |  | 110 |  |  |
| Leu | Ser | Asn | Ile | Pro | Glu | Val | Thr | Glu | Val | Pro | Ser | Phe | Ser | Lys | Glu |
|  |  |  | 115 |  |  |  |  | 120 |  |  |  |  | 125 |  |  |
| Ala | Gln | Ser | Phe | Leu | Gln | Gly | Ile | Ile | Asp | Gly | Phe | Ser | Ile | Asp | Asp |
|  |  | 130 |  |  |  |  | 135 |  |  |  |  | 140 |  |  |  |
| Ala | Leu | Glu | Ile | Lys | Lys | Ile | Glu | Arg | Val | Thr | Asn | His | Asp | Val | Lys |

|     | 145 |     |     |     | 150 |     |     |     | 155 |     |     |     | 160 |
| --- | --- | --- | --- | --- | --- | --- | --- | --- | --- | --- | --- | --- | --- |
| Ala | Val | Glu | Tyr | Phe | Leu | Lys | Gln | Lys | Cys | Glu | Ser | Gln | Pro | Glu | Ile |
|     |     |     |     | 165 |     |     |     |     | 170 |     |     |     | 175 |     |     |
| Ala | Lys | Val | Leu | Glu | Phe | Phe | His | Phe | Ala | Cys | Thr | Ser | Glu | Asp | Ile |
|     |     |     | 180 |     |     |     |     | 185 |     |     |     |     | 190 |     |     |
| Asn | Asn | Leu | Ser | His | Ala | Leu | Met | Leu | Gln | Glu | Ala | Leu | Ser | Ser | Val |
|     |     | 195 |     |     |     |     | 200 |     |     |     |     | 205 |     |     |     |
| Ile | Leu | Pro | Thr | Met | Asp | Glu | Leu | Ile | Lys | Ser | Ile | Ser | Leu | Ile | Ala |
|     | 210 |     |     |     |     | 215 |     |     |     | 220 |     |     |     |     |     |
| Lys | Asn | Phe | Ala | Tyr | Val | Pro | Met | Leu | Ser | Arg | Thr | His | Gly | Gln | Pro |
| 225 |     |     |     |     | 230 |     |     |     |     | 235 |     |     |     |     | 240 |
| Ala | Thr | Pro | Thr | Thr | Leu | Gly | Lys | Glu | Met | Ala | Asn | Phe | Ala | Val | Arg |
|     |     |     |     | 245 |     |     |     |     | 250 |     |     |     |     | 255 |     |
| Leu | Ser | Glu | Glu | Arg | Arg | Tyr | Leu | Ser | Glu | Thr | Lys | Ile | Lys | Gly | Lys |
|     |     |     | 260 |     |     |     |     | 265 |     |     |     |     | 270 |     |     |
| Phe | Ala | Gly | Ala | Val | Gly | Asn | Tyr | Asn | Ala | His | Ile | Ser | Ala | Tyr | Ser |
|     |     |     | 275 |     |     |     |     | 280 |     |     |     |     | 285 |     |     |
| Asn | Ile | Asp | Trp | Pro | His | Val | Ser | Glu | Glu | Phe | Val | Thr | Ser | Leu | Gly |
|     |     | 290 |     |     |     |     | 295 |     |     |     |     | 300 |     |     |     |
| Leu | Thr | Phe | Asn | Pro | Tyr | Val | Thr | Gln | Ile | Glu | Pro | His | Asp | Tyr | Met |
| 305 |     |     |     |     | 310 |     |     |     |     | 315 |     |     |     |     | 320 |
| Ala | Arg | Leu | Phe | Asn | Asn | Ile | Ser | Gln | Phe | Asn | Thr | Ile | Leu | Ile | Asp |
|     |     |     |     | 325 |     |     |     |     | 330 |     |     |     |     | 335 |     |
| Phe | Asp | Arg | Asp | Ile | Trp | Ser | Tyr | Ile | Ser | Leu | Gly | Tyr | Phe | Lys | Gln |
|     |     |     | 340 |     |     |     |     | 345 |     |     |     |     | 350 |     |     |
| Thr | Thr | Lys | Ala | Gly | Glu | Ile | Gly | Ser | Ser | Thr | Met | Pro | His | Lys | Val |
|     |     | 355 |     |     |     |     | 360 |     |     |     |     | 365 |     |     |     |
| Asn | Pro | Ile | Asp | Phe | Glu | Asn | Ser | Glu | Gly | Asn | Leu | Gly | Lys | Ala | Asn |
|     | 370 |     |     |     |     | 375 |     |     |     |     | 380 |     |     |     |     |
| Ala | Glu | Leu | Thr | Phe | Leu | Ser | Met | Lys | Leu | Pro | Ile | Ser | Arg | Met | Gln |
| 385 |     |     |     |     | 390 |     |     |     |     | 395 |     |     |     |     | 400 |
| Arg | Asp | Leu | Thr | Asp | Ser | Thr | Val | Leu | Arg | Asn | Met | Gly | Gly | Ala | Leu |
|     |     |     |     | 405 |     |     |     |     | 410 |     |     |     |     | 415 |     |
| Gly | His | Ser | Leu | Leu | Ala | Tyr | Lys | Ser | Ala | Ile | Gln | Gly | Ile | Gly | Lys |
|     |     |     | 420 |     |     |     |     | 425 |     |     |     |     | 430 |     |     |
| Leu | Gln | Val | Asn | Glu | Ala | Arg | Leu | Lys | Glu | Asp | Leu | Asp | Asp | Asn | Trp |
|     |     | 435 |     |     |     |     | 440 |     |     |     |     | 445 |     |     |     |
| Glu | Val | Leu | Ala | Glu | Pro | Ile | Gln | Thr | Val | Met | Arg | Arg | Tyr | Gly | Val |
|     | 450 |     |     |     |     | 455 |     |     |     |     | 460 |     |     |     |     |
| Pro | Glu | Pro | Tyr | Glu | Lys | Leu | Lys | Glu | Leu | Thr | Arg | Gly | Lys | Ala | Val |
| 465 |     |     |     |     | 470 |     |     |     |     | 475 |     |     |     |     | 480 |
| Asn | Glu | Glu | Thr | Ile | Arg | Thr | Phe | Ile | Lys | Gly | Leu | Glu | Leu | Pro | Ser |
|     |     |     |     | 485 |     |     |     |     | 490 |     |     |     |     | 495 |     |
| Glu | Ala | Lys | Asp | Gln | Leu | Leu | Glu | Leu | Thr | Pro | His | Thr | Tyr | Val | Gly |
|     |     |     | 500 |     |     |     |     | 505 |     |     |     |     | 510 |     |     |
| Ala | Ala | Ala | Ala | Leu | Ala | Leu | Ala | Val | Asp | Glu | Ala | Leu | His | Leu | Gly |
|     |     |     | 515 |     |     |     |     | 520 |     |     |     |     | 525 |     |     |
| His |

( 2 ) INFORMATION FOR SEQ ID NO:3:

( i ) SEQUENCE CHARACTERISTICS:
( A ) LENGTH: 450 base pairs
( B ) TYPE: nucleic acid
( C ) STRANDEDNESS: single (D) TOPOLOGY: linear (ii) MOLECULE TYPE: cDNA (ix) FEATURE:
    (A) NAME/KEY: misc_feature
    (B) LOCATION: 1..450
    (D) OTHER INFORMATION: /note="Partial cDNA of second Arabidopsis gene for Adenylosuccinate Lyase"

(xi) SEQUENCE DESCRIPTION: SEQ ID NO:3:

```
GGCACGAGCG GCACGAGACG ATTTGGATCA TACTTGGGAA GTCCTCGCTG AACCGATACA      60
AACTGTGATG AGGAGATATG GTGTTCCAGA GCCGTATGAG AAGCTGAAGG AGCTAACAAG     120
AGGAAGAGCT GTGAATGAAG AAAGCATTAG AAAGTTTATT AAAAGTTTGG AATTGCCTGA     180
AGAAGCAAAA GACCAACTTT TGAAGCTAAC TCCACACACA TATGTTGGCG CTGCTGCTGC     240
ATTGGCACTA GCCGTGGATG ATGCTGTGCA CTTGGGACAT TAATAATATG ATCATATTGG     300
TGTAGATGAT TCTGCTTGTT GTATTATGAT TTTCTTTTCC CAAATCCAAT GGGAAAACAA     360
GAATCAGTTT ATTGATCGTT GTGTTATGTT TCTTTTTTGA GTTTCAATTA ATCTAGAGCC     420
TCGTTTTGAT CCNAAAAAAA AAAAAAAAA                                       450
```

(2) INFORMATION FOR SEQ ID NO:4:

(i) SEQUENCE CHARACTERISTICS:
        (A) LENGTH: 1659 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (ix) FEATURE:
        (A) NAME/KEY: CDS
        (B) LOCATION: 38..1423
        (D) OTHER INFORMATION: /product="Maize ADSL"
        / note="Sequence does not include a presumed chloroplast transit peptide"

(xi) SEQUENCE DESCRIPTION: SEQ ID NO:4:

```
GGCACGAGGC TTGCCGGACC ACGACACGTT CTGCTTG ATG GCG CTC TCG CCG CTG        55
                                        Met Ala Leu Ser Pro Leu
                                         1               5

GAC GGG CGG TAC GAT CGC TTC GTC AAG GAG CTG ATG CCC TTT TTC AGC        103
Asp Gly Arg Tyr Asp Arg Phe Val Lys Glu Leu Met Pro Phe Phe Ser
         10                  15                  20

GAG TTC GGC CTA ATC AGA TAC CGC GTT CTC ATC GAG ATC AAG TGG CTA        151
Glu Phe Gly Leu Ile Arg Tyr Arg Val Leu Ile Glu Ile Lys Trp Leu
             25                  30                  35

CTG AAA CTT TCT CAA ATT CCT GAG ATC ACT GAG GTG CCT CAG TTC AGC        199
Leu Lys Leu Ser Gln Ile Pro Glu Ile Thr Glu Val Pro Gln Phe Ser
     40                  45                  50

AAG GAA GCT CAG TCC TTG TTG AAT GCC ATT ATT GAG AAT TTT TGC ATA        247
Lys Glu Ala Gln Ser Leu Leu Asn Ala Ile Ile Glu Asn Phe Cys Ile
 55                  60                  65                  70

GAT GAT GCA AAA GAA GTT AAG AAA ATC GAG AAA GTA ACC AAC CAT GAC        295
Asp Asp Ala Lys Glu Val Lys Lys Ile Glu Lys Val Thr Asn His Asp
                 75                  80                  85

GTG AAA GCC GTG GAG TAC TTT CTG AAG CAA AGG TGC AGC TCA AAT CCA        343
Val Lys Ala Val Glu Tyr Phe Leu Lys Gln Arg Cys Ser Ser Asn Pro
             90                  95                 100

GAG ATT GCA AAG GTG TCG GAA TTC TTC CAT TTT GGT TGT ACC TCT GAA        391
Glu Ile Ala Lys Val Ser Glu Phe Phe His Phe Gly Cys Thr Ser Glu
```

```
             105                         110                          115
GAT ATT AAC AAT CTA TCA CAT GCA TTG GCT TTG AAA GAG GGG GTA AAT                439
Asp Ile Asn Asn Leu Ser His Ala Leu Ala Leu Lys Glu Gly Val Asn
    120             125                 130

AAA GTT ATG TTC CCT GCC ATG ATC GAT CTA TGC AGA GCA ATG TGT TCC                487
Lys Val Met Phe Pro Ala Met Ile Asp Leu Cys Arg Ala Met Cys Ser
135             140                 145                 150

TTG GCA ACA CAA AAT TCA GGC TAC CCT ATG TTG GCT CGA ACT CAT GGG                535
Leu Ala Thr Gln Asn Ser Gly Tyr Pro Met Leu Ala Arg Thr His Gly
                155                 160                 165

CAG GCA GCA TCA CCA ACA ACT GTG GGA AAG GAG ATG GCA AAC TTC GCG                583
Gln Ala Ala Ser Pro Thr Thr Val Gly Lys Glu Met Ala Asn Phe Ala
            170             175                 180

GGC AGA TTA TCT GAT ATA GGA AAG AGT TTC TCA GAG GTG AAG ATA CTA                631
Gly Arg Leu Ser Asp Ile Gly Lys Ser Phe Ser Glu Val Lys Ile Leu
            185             190                 195

GGG AAA TTT GCT GGC GCT GTT GGC AAT TAC AAT GCT GAT GTG GTT GCA                679
Gly Lys Phe Ala Gly Ala Val Gly Asn Tyr Asn Ala Asp Val Val Ala
        200             205                 210

TAT CCT GAA GTT GAC TGG CCT AAG GTG GCA GAA GAG TTT GTT AGA TCC                727
Tyr Pro Glu Val Asp Trp Pro Lys Val Ala Glu Glu Phe Val Arg Ser
215                 220                 225                 230

TTG GGT TTG CAG TTT AAT CCC TAT GTT ACT CAG ATT GAG CCT CAT GAC                775
Leu Gly Leu Gln Phe Asn Pro Tyr Val Thr Gln Ile Glu Pro His Asp
                235                 240                 245

TAC ATA TCA AAG CTC TTC AAT CTA TTC ACC CAG TTT AAC AAT GTG TTG                823
Tyr Ile Ser Lys Leu Phe Asn Leu Phe Thr Gln Phe Asn Asn Val Leu
        250                 255                 260

ACT GAT TTT GAT AGA GAC ATG TGG TCC TAT ATA TCA TTA GGC TAC TTC                871
Thr Asp Phe Asp Arg Asp Met Trp Ser Tyr Ile Ser Leu Gly Tyr Phe
        265                 270                 275

AAG CAG ATA CCA AAG GCT GGT GAA GTT GGT TCT TCC ACT ATG CCT CAT                919
Lys Gln Ile Pro Lys Ala Gly Glu Val Gly Ser Ser Thr Met Pro His
        280                 285                 290

AAA ATC AAC CCC ATT GAT TTT GAA AAT AGT GAT GGC AAT TTA TGT CAA                967
Lys Ile Asn Pro Ile Asp Phe Glu Asn Ser Asp Gly Asn Leu Cys Gln
295                 300                 305                 310

GCG AAT TCT ATA TTG TCT GGT ATA AGC ATG AAA CTA CCA ATA TCC CGG               1015
Ala Asn Ser Ile Leu Ser Gly Ile Ser Met Lys Leu Pro Ile Ser Arg
                315                 320                 325

TTG CAG CGT GAC CTA ACA GAC TCG ACT GTT TTG AGA AAC CTG GGT ATG               1063
Leu Gln Arg Asp Leu Thr Asp Ser Thr Val Leu Arg Asn Leu Gly Met
            330                 335                 340

GGA TTA GGT CAT TCT CTA TTG GCT TAC AAA GCT ACC ATG CGT GGA ATC               1111
Gly Leu Gly His Ser Leu Leu Ala Tyr Lys Ala Thr Met Arg Gly Ile
        345                 350                 355

AGC AAG GTT CAG TTG AAT GAA TCA CGT TTA GCT GAA GAC CTG GAG CAA               1159
Ser Lys Val Gln Leu Asn Glu Ser Arg Leu Ala Glu Asp Leu Glu Gln
    360                 365                 370

ACT TGG GAG GTC CTT GCT GAG CCA ATA CAG ACA GTG ATG CGA AGA TAT               1207
Thr Trp Glu Val Leu Ala Glu Pro Ile Gln Thr Val Met Arg Arg Tyr
375                 380                 385                 390

GGG ATA CCT GAA CCT TAT GAG AAG CTG AAG GAA CTG ACG AGA GGC CAA               1255
Gly Ile Pro Glu Pro Tyr Glu Lys Leu Lys Glu Leu Thr Arg Gly Gln
                395                 400                 405

GCT GTC ACC AAG GAC AGC ATG CAG CAA TTC ATT AAT GGT CTA GAC ATA               1303
Ala Val Thr Lys Asp Ser Met Gln Gln Phe Ile Asn Gly Leu Asp Ile
            410                 415                 420

CCG GAG GAG GTT CGA TCG AAG CTT TCG AAG CTA ACC CCG CAT TCC TAC               1351
Pro Glu Glu Val Arg Ser Lys Leu Ser Lys Leu Thr Pro His Ser Tyr
```

-continued

```
                425                    430                         435
ACT GGG CTA GCG GAG GAT TTG GCC AGA GAC ATC GAG AAG TGG GTT GAT          1399
Thr Gly Leu Ala Glu Asp Leu Ala Arg Asp Ile Glu Lys Trp Val Asp
        440                 445                 450

CTT GAA TCT GGA TTT CAG ATC AAG TGAGCTCCCA TTGACAACA ATGGAGAAAA         1453
Leu Glu Ser Gly Phe Gln Ile Lys
455                 460

TAAATAACAG ACGGGAACCC TAGGAAACGA GAATCCAATG CTGGAACCAA GGTGCCGTTT       1513

GGTTCACAAA TTTGTAACGT AATGGGTAAC GAATAACGTT AAATCATGTT TGTTTAGTC        1573

CAACTGTAAT CGAATACTAC ACTAAAAATT GATACCAGCC TATTCCAATT AAAAAAAAA        1633

AAAAAAAAAA AAAAAAAAA AAAAA                                              1659
```

( 2 ) INFORMATION FOR SEQ ID NO:5:

( i ) SEQUENCE CHARACTERISTICS:
( A ) LENGTH: 462 amino acids
( B ) TYPE: amino acid
( D ) TOPOLOGY: linear ( i i ) MOLECULE TYPE: protein ( x i ) SEQUENCE DESCRIPTION: SEQ ID NO:5:

```
Met Ala Leu Ser Pro Leu Asp Gly Arg Tyr Asp Arg Phe Val Lys Glu
 1               5                  10                  15

Leu Met Pro Phe Phe Ser Glu Phe Gly Leu Ile Arg Tyr Arg Val Leu
            20                  25                  30

Ile Glu Ile Lys Trp Leu Leu Lys Leu Ser Gln Ile Pro Glu Ile Thr
         35                  40                  45

Glu Val Pro Gln Phe Ser Lys Glu Ala Gln Ser Leu Leu Asn Ala Ile
     50                  55                  60

Ile Glu Asn Phe Cys Ile Asp Asp Ala Lys Glu Val Lys Lys Ile Glu
 65                  70                  75                  80

Lys Val Thr Asn His Asp Val Lys Ala Val Glu Tyr Phe Leu Lys Gln
                85                  90                  95

Arg Cys Ser Ser Asn Pro Glu Ile Ala Lys Val Ser Glu Phe Phe His
            100                 105                 110

Phe Gly Cys Thr Ser Glu Asp Ile Asn Asn Leu Ser His Ala Leu Ala
        115                 120                 125

Leu Lys Glu Gly Val Asn Lys Val Met Phe Pro Ala Met Ile Asp Leu
    130                 135                 140

Cys Arg Ala Met Cys Ser Leu Ala Thr Gln Asn Ser Gly Tyr Pro Met
145                 150                 155                 160

Leu Ala Arg Thr His Gly Gln Ala Ala Ser Pro Thr Thr Val Gly Lys
                165                 170                 175

Glu Met Ala Asn Phe Ala Gly Arg Leu Ser Asp Ile Gly Lys Ser Phe
            180                 185                 190

Ser Glu Val Lys Ile Leu Gly Lys Phe Ala Gly Ala Val Gly Asn Tyr
        195                 200                 205

Asn Ala Asp Val Val Ala Tyr Pro Glu Val Asp Trp Pro Lys Val Ala
    210                 215                 220

Glu Glu Phe Val Arg Ser Leu Gly Leu Gln Phe Asn Pro Tyr Val Thr
225                 230                 235                 240

Gln Ile Glu Pro His Asp Tyr Ile Ser Lys Leu Phe Asn Leu Phe Thr
                245                 250                 255

Gln Phe Asn Asn Val Leu Thr Asp Phe Asp Arg Asp Met Trp Ser Tyr
            260                 265                 270
```

```
Ile  Ser  Leu  Gly  Tyr  Phe  Lys  Gln  Ile  Pro  Lys  Ala  Gly  Glu  Val  Gly
          275                      280                      285

Ser  Ser  Thr  Met  Pro  His  Lys  Ile  Asn  Pro  Ile  Asp  Phe  Glu  Asn  Ser
     290                      295                     300

Asp  Gly  Asn  Leu  Cys  Gln  Ala  Asn  Ser  Ile  Leu  Ser  Gly  Ile  Ser  Met
305                      310                     315                          320

Lys  Leu  Pro  Ile  Ser  Arg  Leu  Gln  Arg  Asp  Leu  Thr  Asp  Ser  Thr  Val
                325                      330                           335

Leu  Arg  Asn  Leu  Gly  Met  Gly  Leu  Gly  His  Ser  Leu  Leu  Ala  Tyr  Lys
               340                      345                          350

Ala  Thr  Met  Arg  Gly  Ile  Ser  Lys  Val  Gln  Leu  Asn  Glu  Ser  Arg  Leu
          355                      360                     365

Ala  Glu  Asp  Leu  Glu  Gln  Thr  Trp  Glu  Val  Leu  Ala  Glu  Pro  Ile  Gln
     370                      375                     380

Thr  Val  Met  Arg  Arg  Tyr  Gly  Ile  Pro  Glu  Pro  Tyr  Glu  Lys  Leu  Lys
385                      390                     395                          400

Glu  Leu  Thr  Arg  Gly  Gln  Ala  Val  Thr  Lys  Asp  Ser  Met  Gln  Gln  Phe
               405                      410                          415

Ile  Asn  Gly  Leu  Asp  Ile  Pro  Glu  Glu  Val  Arg  Ser  Lys  Leu  Ser  Lys
               420                      425                          430

Leu  Thr  Pro  His  Ser  Tyr  Thr  Gly  Leu  Ala  Glu  Asp  Leu  Ala  Arg  Asp
          435                      440                     445

Ile  Glu  Lys  Trp  Val  Asp  Leu  Glu  Ser  Gly  Phe  Gln  Ile  Lys
     450                      455                     460
```